(12) United States Patent
Engelman et al.

(10) Patent No.: US 8,716,216 B2
(45) Date of Patent: May 6, 2014

(54) HUMAN IMMUNOSUPPRESSIVE PROTEIN

(75) Inventors: Robert W. Engelman, Tampa, FL (US); William R. Gower, Seffner, FL (US); Paul R. Sanberg, Spring Hill, FL (US)

(73) Assignee: University of South Florida, Tampa, FL (US)

( * ) Notice: Subject to any disclaimer, the term of this patent is extended or adjusted under 35 U.S.C. 154(b) by 914 days.

(21) Appl. No.: 12/118,675

(22) Filed: May 9, 2008

(65) Prior Publication Data

US 2008/0280812 A1    Nov. 13, 2008

Related U.S. Application Data

(62) Division of application No. 10/621,061, filed on Jul. 16, 2003, now Pat. No. 7,388,076.

(60) Provisional application No. 60/396,928, filed on Jul. 16, 2002.

(51) Int. Cl.
*A61K 38/00* (2006.01)
*C07K 14/47* (2006.01)
*C07K 14/55* (2006.01)

(52) U.S. Cl.
USPC ............ 514/1.1; 530/350; 435/325; 435/368; 435/41

(58) Field of Classification Search
None
See application file for complete search history.

(56) References Cited

U.S. PATENT DOCUMENTS 6,254,865 B1 * 7/2001 Freed et al. .................. 424/93.7
2002/0192194 A1 * 12/2002 McGrogan et al. ........ 424/93.21

OTHER PUBLICATIONS

Gower et al., hNT neurons express an immunosuppressive protein that blocks T-lymphocyte proliferation and interleukin-2 production. Journal of Neuroimmunology 125 (2002) 103-113.*

* cited by examiner

*Primary Examiner* — Jeffrey Stucker
*Assistant Examiner* — Aurora M Fontainhas
(74) *Attorney, Agent, or Firm* — Michele L. Lawson; Robert Varkonyi; Smith & Hopen, P. A.

(57) ABSTRACT

A composition of an immunosuppressant protein (HISP) which is achieved by the steps of obtaining supernatant from hNT neuronal cells; exposing the supernatant to preparative polyacrylamide gel; placing the active isoelectric fraction on a Blue Sepharose column to bind albumin; and collecting the free fraction containing the concentrated, isolated HISP. The HISP is anionic, has a molecular weight of 40-100 kDa, an isoelectric point of about 4.8 and is obtained from the supernatant of hNT cells. HISP can suppress proliferation of responder peripheral blood mononuclear cells in allogeneic mixed lymphocyte cultures; HISP can suppress T-cell proliferation and IL-2 production in response to phorbol 12-myristate 13-acetate (PMA), ionomycin and concanavalin-A. HISP does not act through the T-cell receptor-CD3 complex or via altered accessory signal cells.

12 Claims, 5 Drawing Sheets

HUMAN IMMUNOSUPPRESSIVE PROTEIN

CROSS REFERENCE TO RELATED APPLICATIONS

Figure 1:
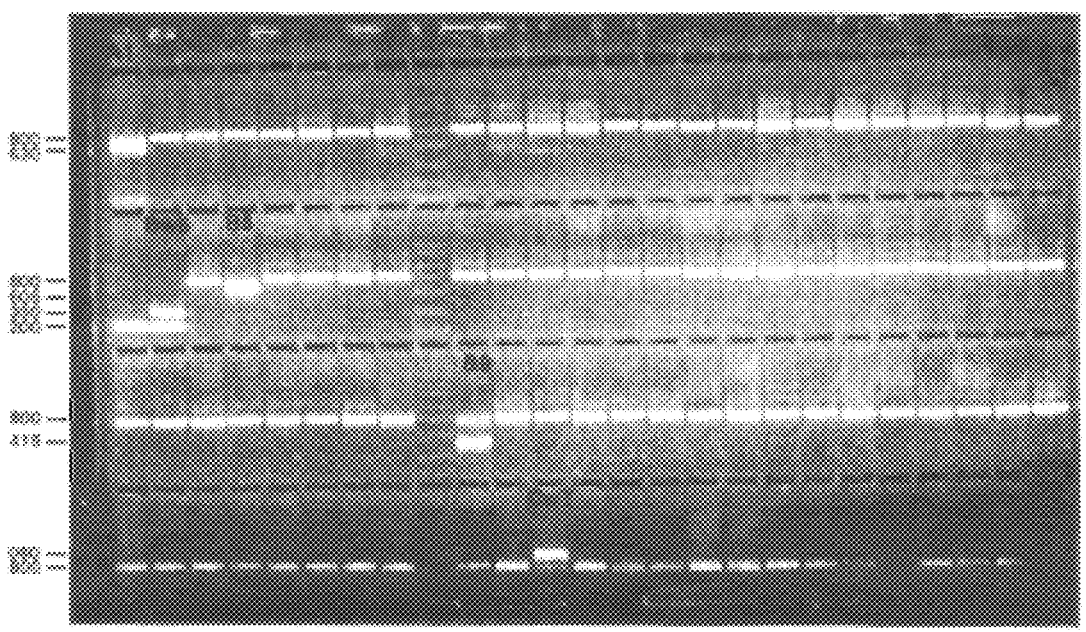

This application is a divisional application of pending U.S. Ser. No. 10/621,061, filed Jul. 16, 2003, which claims the benefit of U.S. Provisional Application No. 60/396,928, filed Jul. 16, 2002.

STATEMENT REGARDING FEDERALLY SPONSORED RESEARCH OR DEVELOPMENT

Some of the work disclosed herein was supported by Small Business Technology Research Grant No. 1-R41-AI50367-01 from the National Institute of Allergy and Infectious Diseases. The government has certain rights in this invention.

BACKGROUND

1. Technical Field

The invention is in the fields of drug therapy; more specifically, the invention encompasses a protein for immunosuppression.

2. The Prior Art

The central nervous system (CNS) actively maintains immune privilege (Carson and Sutcliffe, 1999; Fabry et al., 1994), in part by restricting immune cell access (Goldstein and Betz, 1986; Hickey et al., 1991), having limited afferent antigen drainage (Weller et al., 1996; Cserr and Knopf, 1992), locally suppressing immune responsiveness (Irani et al., 1996; Irani et al., 1997), guiding the recruitment and differentiation of effector cell phenotypes (Aloisi et al., 1998; Carson et al., 1999), and possessing weak antigen presenting cells (Carson et al., 1998).

Neurons may directly modulate immune responsiveness. Absence of constitutive neuronal MHC expression may limit anti-neuronal cytotoxic T-cell effector mechanisms (Rall, 1998). Glycosphingolipids known as gangliosides are enriched within neurons, can be shed from the cell surface, are immunosuppressive, and may contribute to immune privilege (Irani et al., 1996; Rall, 1998). Gangliosides suppress the expression of MHC molecules (Massa, 1993), the proliferation of T-cells, and the production of IL-2 (Irani et al., 1996; Irani et al., 1997; Bergelson, 1995; Robb, 1986; Dyatlov-itskaya and Bergelson, 1987).

The therapeutic approach of transfecting and transplanting neurons to ameliorate neurological deficits requires a defined, preferably clonal source of differentiated human neurons amenable to efficient transfection and sustained expression of therapeutic genes (Trojanowski et al., 1997; Cook et al., 1994). A therapeutic effect is anticipated should the engrafted cells retain a neuronal phenotype, functionally integrate, and deliver a sustained level of therapeutically relevant protein to the affected region of the brain (Cook et al., 1994). This approach has evolved from trials utilizing neuronal isolates of the embryonic ventral mesencephalon (Kordower et al., 1995; Bjorklund, 1992; Perlow et al., 1979), modified neuronal progenitors (Sabate et al., 1995), neurons (Anton et al., 1994), or fibroblasts (Fisher et al., 1991). Ganglioside shedding and the absence of MHC expression may favor resistance of the neuronal graft to MHC-restricted T-cell attack (Lampson and Siegel, 1988).

Embryonic neurons as grafts are limited by their heterogeneity, expense, scarcity, diminishing viability over time, and refractoriness to standard transfection techniques (Cook et al., 1994; Meichsner et al., 1993). A promising alternative neuron, which is amenable to transfection, is derived from the embryonal carcinoma cell line Ntera2/D1, a putative neuronal progenitor (Cook et al., 1994; Andrews et al., 1984). Ntera2/D1 differentiate in response to treatment with all-trans-retinoic acid into a mixture of cells, including postmitotic cells with a neuronal phenotype (Andrews, 1984; Pleasure et al., 1992; Pleasure and Lee, 1993). Cultures are selectively enriched for Ntera2/D1-derived neurons (designated hNT neurons) by inhibiting the non-neuronal cells with mitotic inhibitors, and by replating hNT neurons on poly-D-lysine plus laminin, which encourages growth of polarized processes. In this manner, cultures comprised of >90% hNT neurons are prepared (Cook et al., 1994).

hNT neurons have identifiable axons and dendrites (Andrews, 1984), retain a plasticity to regenerate and extend neurites after multiple replatings in vitro (Cook et al., 1994), and express neurofilaments characteristic of neuronal development and the adult CNS (Andrews, 1984; Lee and Andrews, 1986). hNT neurons synthesize neurotransmitters, express the catecholamine biosynthetic enzyme tyrosine hydroxylase, and excrete the dopamine metabolite homovanillic acid (Zeller and Strauss, 1995; Iacovitti and Stull, 1997). Transplanted hNT neurons are capable of long-term functional integration (Kleppner et al., 1995), are nontumorigenic (Trojanowski et al., 1997), and can correct behavioral deficits in the lesioned rodent (Borlongan et al., 1998).

Although a therapeutic potential of hNT neuronal grafts has been implied, a paucity of data exists regarding its MHC and immunological features. Retinoic acid-induced differentiation of Ntera2/D1 causes the produced hNT neurons to express MHC class I and $\beta$-2 microglobulin molecules (Segars et al., 1993), but whether hNT neurons express a discernable MHC phenotype that can activate allogeneic immunocytes has not been determined. An increase in the expression of gangliosides (e.g., $GD_3$ and $GT_3$) and the glycolipid sialyltransferases that contribute to their synthesis occurs during the differentiation of some embryonal carcinoma cells (Chen et al., 1989; Osania et al., 1997). Whether hNT neurons can modulate immune responses and shed gangliosides at immunosuppressive levels have not been determined. Some CNS neoplasms (e.g., gliomas) express immunosuppressive levels of transforming growth factor-$\beta$. (TGF-$\beta$) (Weller and Fontana, 1995). TGF-$\beta$ inhibits T-cell proliferation by suppressing IL-2-mediated proliferative signals (Ahuja et al., 1993). Retinoic acid treatment increases TGF-$\beta$ expression during murine embryogenesis (Mahmood et al., 1995), and during embryonal carcinoma cell differentiation (Rizzino et al., 1983), but whether hNT neurons express immunosuppressive levels of TGF-$\beta$ has not been determined.

SUMMARY OF THE INVENTION

In one embodiment, there is disclosed a method for purifying an immunosuppressant protein (HISP) which has the following steps: a) obtaining supernatant from hNT cells; b) exposing the supernatant to preparative polyacrylamide gel electrophoresis to produce 20 isoelectric fractions, including active isoelectric fraction #10; c) placing the active isoelectric fraction on a Blue Sepharose column to bind albumin; and d) collecting the free fraction containing the concentrated, isolated HISP.

Also disclosed is the compound produced by claim 1.

In another embodiment, there is a method of treating inflammation, the method comprising administering an effective amount of an immunosuppressant protein (HISP).

In yet another embodiment, there is an isolated immunosuppressant protein (HISP), the protein comprising an anionic protein and having a molecular weight of 40-100 kDa; having an isoelectric point of about 4.8; being obtained from hNT cell supernatant; not being obtained from NCCIT embryonal carcinoma cells, T98G glioblastoma cells or THP-1 monocytic leukemia cells; losing activity when treated with heat, pH 2, pH 11, or mixed with trypsin or carboxypeptidase; losing no activity when incubated with neuraminidase; being capable of suppressing proliferation of responder peripheral blood mononuclear cells in allogeneic mixed lymphocyte cultures; being capable of suppressing T-cell proliferation and IL-2 production in response to phorbol 12-myristate 13-acetate (PMA), ionomycin and concanavalin-A; being capable of maintaining T cells in a quiescent $G_0/G_1$ state without lowering their viability; not binding to heparin-sepharose CL-B gel; not binding to albumin-binding resin Blue Sepharose; concentrating with YM10 ultrafiltration; and not acting through the T-cell receptor-CD3 complex or via altered accessory signal cells.

BRIEF DESCRIPTION OF THE DRAWING FIGURES

FIG. 1 shows the result of ethidium bromide-stained gel electrophoresis of the amplified products of MHC class I specific polymerase chain reactions using Ntera2/D1 genomic DNA as template revealed products of 630 (A1), 350 (Bw6), 605 and 415 (B8), and 1060 (Cw7) base pairs, indicating a MHC class I genotype of A1 B8 Bw6 Cw7.

Figure 2:
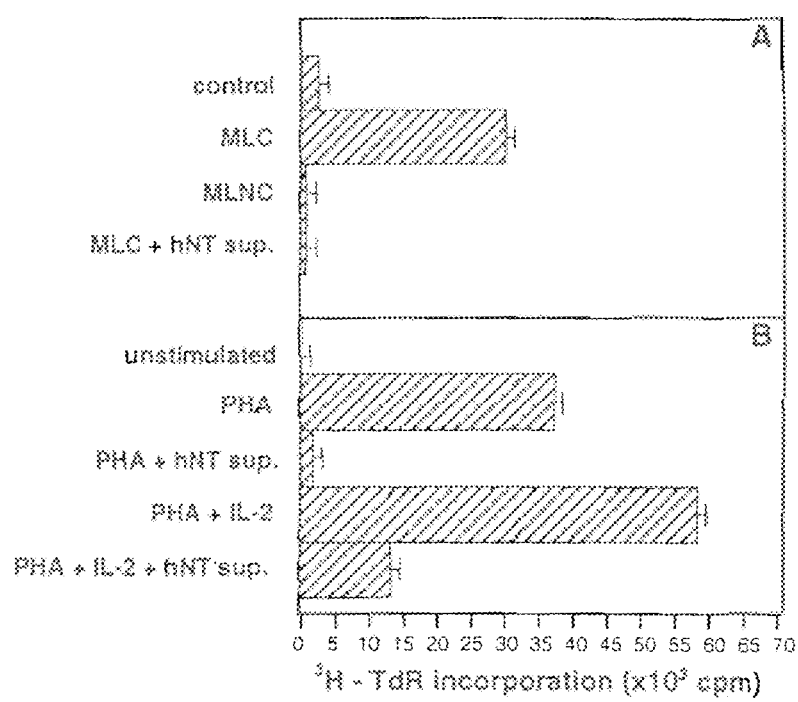

FIGS. 2A and 2B are graphs showing the quantity of $^3$H-TdR incorporation by control and PHA-activated cells. FIG. 2A shows that the hNT neurons did not activate allogeneic PBMC to proliferate in mixed lymphocyte-neuron cultures (MLNC) compared to the proliferation of allogeneic mixed lymphocyte cultures (MLC). When hNT supernatant was added the proliferation of allogeneic MLC was suppressed to basal levels comparable to those of unstimulated controls. Values are mean±SD. FIG. 2B shows that the hNT supernatant significantly suppressed the proliferation of PHA-stimulated PBMC. Supplemental IL-2 augmented the PHA-induced proliferation of PBMC, but did not rescue the T-lymphocytes suppressed by exposure to hNT supernatant. Values are mean±SD.

Figure 3:
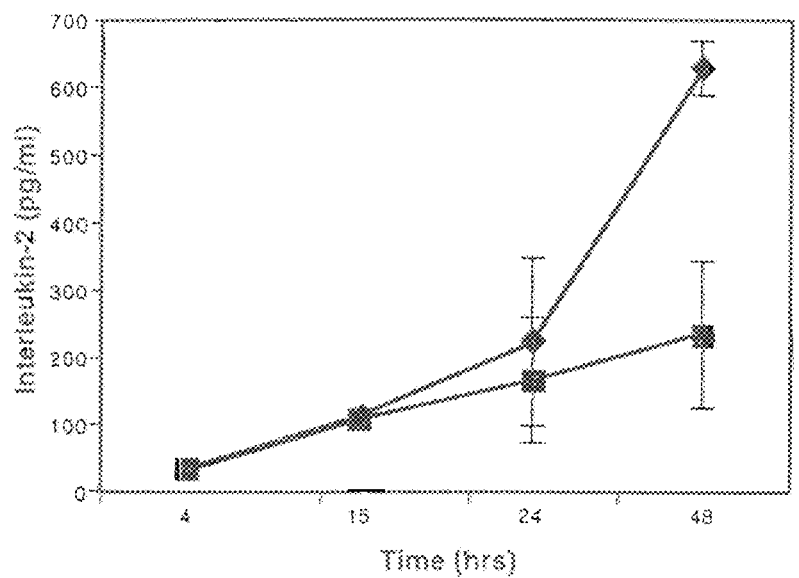

FIG. 3 shows that the mean±SD levels of IL-2 expressed by PHA-stimulated PBMC were significantly less when cultured in the presence of hNT supernatant (■) compared to controls (◇), 48 hours after mitogen stimulation (p<0.01).

Figure 4:
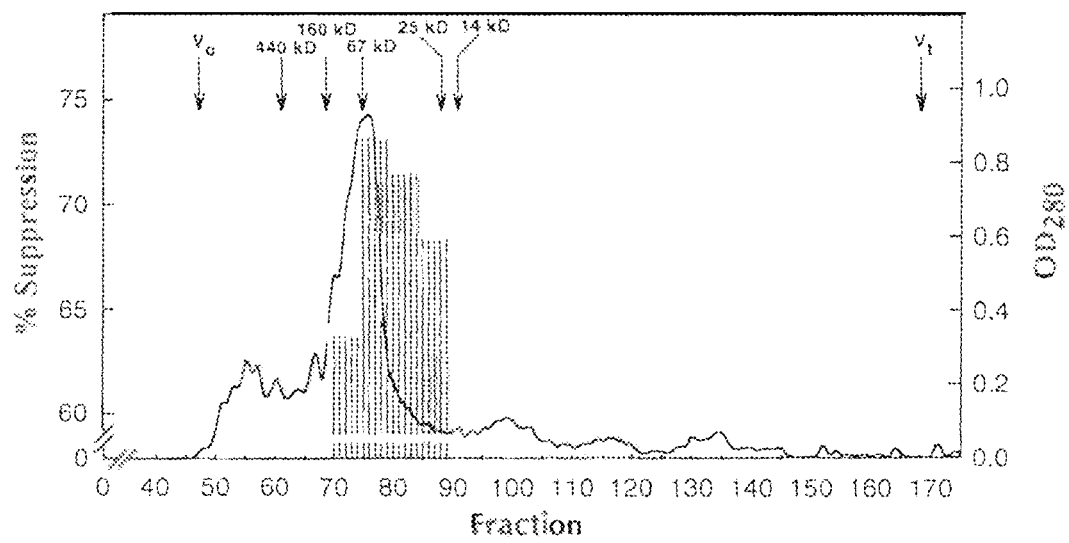

FIG. 4 shows the results when hNT supernatant was concentrated and the concentrate fractionated. The fractions from gel filtration were evaluated for protein content (continuous tracing), and assessed for an ability to suppress the PHA-stimulated proliferation of T-cells (vertical bars). Suppression of T-cell proliferation was greatest in fractions corresponding to a mass of 40-100 kDa.

Figure 5:
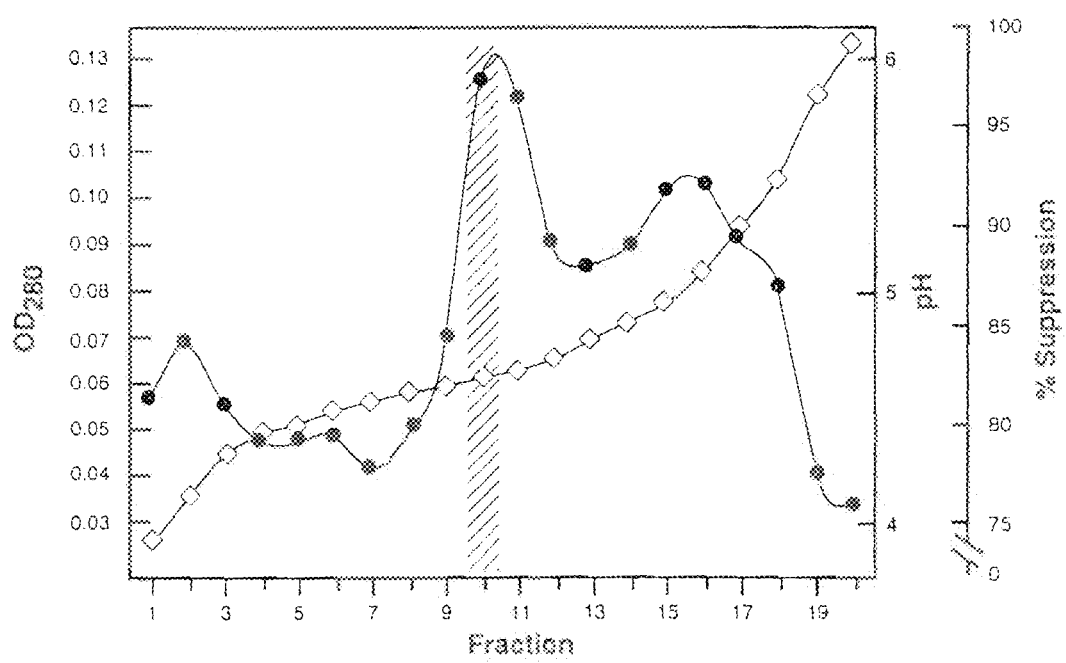

FIG. 5 shows the peak active fraction of hNT supernatant from gel filtration which underwent isoelectric focusing using a narrow ampholyte range of pH 4-6 (◇). Isoelectric tractions were assessed for protein content at 280 nm (●). Of the twenty fractions collected and evaluated, only isoelectric fraction #10 (IEF-10) significantly suppressed the proliferation of PBMC induced by PHA (vertical slashed bar) (p<0.01). Values are mean±SD.

DETAILED DESCRIPTION OF A PREFERRED EMBODIMENT

In light of the therapeutic potential of hNT neuronal grafts, we evaluated hNT for its MHC and immunological characteristics, and for evidence of neuronal regulation of immune cells in vitro. During this evaluation, we quite serendipitously discovered a novel hNT neuron-expressed immunosuppressive protein (HISP) with characteristics unlike gangliosides or TGF-.beta., which is potently suppressive of T-cell activation, proliferation, and the production of IL-2. Consequently, hNT neuronal grafts may prove to be both therapeutic and self-protective, engrafted alone, or as co-grafts with other neurons.

Ntera2/D1 cells had an A1 B8 Bw6 Cw7 DR3 DR52 major histocompatibility complex (MHC) genotype. Its neuronal derivative, hNT neurons, expressed A1 B8 Bw6 MHC class I molecules, but did not activate, and its hNT supernatant suppressed allogeneic mixed lymphocyte cultures (MLC)>98% (p<0.01), phytohemagglutinin (PHA)-activated T-cell proliferation >87% (p<0.01), even 48 hours after stimulation, suppressed phorbol 12-myristate 13-acetate (PMA)/ionomycin-induced T-cell proliferation >99% (p<0.001), and reduced interleukin-2 (IL-2) production (p<0.01), while maintaining T-cells in a quiescent $G_0/G_1$ state without lowering their viability. This immunosuppressive activity was attributed to a 40-100 kDa anionic hNT protein with an isoelectric point of 4.8.

Immunosuppressant as used herein is a substance that prevents or attenuates immunologic phenomena. For example, such immunologic phenomena include inflammation, autoimmunity, GVHD and graft rejection. Examples of currently available immunosuppressants include but are not limited to cyclosporine A, cyclophosphamide, prednisone and tacrolimus (FK506).

"Beneficial effect" is an observable improvement over the baseline clinically observable signs and symptoms. For example, a beneficial effect could include improvements in graft survival, decreased inflammation or improvements in the disease treated.

"Mammal" includes humans and other mammals that would reasonably benefit from treatment of immune and inflammation disorders, including pets like dogs, cats and horses.

An "active fragment" of the immunosuppressant protein is a peptide or polypeptide that comprises a fragment of the protein and retains at least one physiological activity of the immunosuppressant protein, e.g., by acting as a suppressor of the T lymphocyte activation reaction.

A peptide of the present invention includes, but is not limited to, those containing, as a primary amino acid sequence, all or part of the amino acid sequence of the immunosuppressant protein including altered sequences in which functionally equivalent amino acid residues are substituted for residues within the sequence resulting in a conservative amino acid substitution. Such alterations define the term "a conservative substitution" as used herein. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight, as determined by polyacrylamide gel electrophoresis, or isoelectric point.

Particularly preferred conservative substitutions are as follows: Lys for Arg and vice versa such that a positive charge may be maintained; Glu for Asp and vice versa such that a negative charge may be maintained; Ser for Thr such that a free —OH can be maintained; and Gln for Asn such that a free $NH_2$ can be maintained.

A polypeptide is a polymer of amino acid residues. As used herein, unless otherwise specifically indicated, the terms "polypeptide" and "protein" are used interchangeably with each other and with the term "peptide" though, the term "peptide" is preferably used for smaller amino acid polymers, e.g., less than 50 amino acids and/or for fragments of a protein that are missing at least about one third of their amino acids.

One skilled in the art can readily adapt the nucleic acid sequences of the invention to any system that is capable of producing nucleic acids to produce the nucleic acids of the invention. The nucleic acids of the invention, which may optionally comprise a detectable label, may be prepared as cDNA clones, genomic clones, RNA transcribed from either cDNA or genomic clones, synthetic oligonucleotides, and/or synthetic amplification products resulting, e.g., from PCR. The nucleic acids of the invention may be prepared in either single- or double-stranded form.

Synthetic peptides prepared using the well known techniques of solid phase, liquid phase, or peptide condensation techniques, or any combination thereof, can include natural and unnatural amino acids. Amino acids used for peptide synthesis may be standard Boc ($N_\alpha$-amino protected $N_\alpha$-t-butyloxycarbonyl) amino acid resin with the standard deprotecting, neutralization, coupling and wash protocols of the original solid phase procedure of Merrifield [J. Am. Chem. Soc, 85:2149-2154 (1963)], or the base-labile $N_\alpha$-amino protected 9-fluorenylmethoxycarbonyl (Fmoc) amino acids first described by Carpino and Han [J. Org. Chem., 37:3403-3409 (1972)]. Both Fmoc and Boc $N_\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N_\alpha$-protecting groups that are familiar to those skilled in this art. Solid phase peptide synthesis may be accomplished by techniques familiar to those in the art and provided, for example, in Stewart and Young, 1984, Solid Phase Synthesis, Second Edition, Pierce Chemical Co., Rockford, III; Fields and Noble, 1990, Int. J. Pept. Protein Res. 35:161-214, or using automated synthesizers, such as sold by ABS. Thus, the ARF-p19 peptides of the invention may comprise D-amino acids, a combination of D- and L-amino acids, and various "designer" amino acids (e.g., 13-methyl amino acids, $C_\alpha$-methyl amino acids, and $N_\alpha$-methyl amino acids, etc.) to convey special properties. Synthetic amino acids include omithine for lysine, fluorophenylalanine for phenylalanine, and norleucine for leucine or isoleucine. Additionally, by assigning specific amino acids at specific coupling steps, α-helices, β-turns, β-sheets, γ-turns, and cyclic peptides can be generated.

In another embodiment, the therapeutic compound can be delivered in a vesicle, in particular a liposome [see Langer, Science, 249:1527-1533 (1990); Treat et al., in Liposomes in the Therapy of Infectious Disease and Cancer, Lopez-Berestein and Fidler (eds.), Liss: New York, pp. 353-365 (1989); Lopez-Berestein, ibid., pp. 317-327; see generally ibid.]. To reduce its systemic side effects, this may be a preferred method for introducing the immunosuppressant protein.

In yet another embodiment, the therapeutic compound can be delivered in a controlled release system. For example, the polypeptide may be administered using intravenous infusion, an implantable osmotic pump, a transdermal patch, liposomes, or other modes of administration. In one embodiment, a pump may be used [see Langer, supra; Sefton, CRC Crit. Ref. Biomed. Eng., 14:201 (1987); Buchwald et al., Surgery, 88:507 (1980); Saudek et al., N. Engl. J. Med., 321:574 (1989)]. In another embodiment, polymeric materials can be used [see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem., 23:61 (1983): see also Levy et al., Science, 228:190 (1985); During et al., Ann. Neurol., 25:351 (1989); Howard et al., J. Neurosurg., 71:105 (1989)]. In yet another embodiment, a controlled release system can be placed in proximity of the therapeutic target, i.e., a brain tumor, thus requiring only a fraction of the systemic dose [see, e.g., Goodson, in Medical Applications of Controlled Release, supra, vol. 2, pp. 115-138 (1984)]. Preferably, a controlled release device is introduced into a subject in proximity of the site of a tumor. Other controlled release systems are discussed in the review by Langer [Science, 249:1527-1533 (1990)].

Pharmaceutical Compositions. In yet another aspect of the present invention, provided are pharmaceutical compositions of the above. Such pharmaceutical compositions may be for administration for injection, or for oral, pulmonary, nasal or other forms of administration. In general, comprehended by the invention are pharmaceutical compositions comprising effective amounts of a low molecular weight component or components, or derivative products, of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., thimerosal, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., Remington's Pharmaceutical Sciences, 18th Ed. [1990, Mack Publishing Co., Easton, Pa. 18042] pages 1435-1712 which are herein incorporated by reference. The compositions may be prepared in liquid form, or may be in dried powder, such as lyophilized form.

Oral Delivery is contemplated for use herein. Oral solid dosage forms are described generally in Remington's Pharmaceutical Sciences, 18th Ed. 1990 (Mack Publishing Co. Easton, Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013, 556). A description of possible solid dosage forms for the therapeutic is given by Marshall, K. In: Modern Pharmaceutics Edited by G. S. Banker and C. T. Rhodes Chapter 10, 1979, herein incorporated by reference. In general, the formulation includes the immunosuppressant protein (or chemically modified forms thereof) and inert ingredients which allow for protection against the stomach environment, and release of the biologically active material in the intestine.

Also specifically contemplated are oral dosage forms of the above derivatized component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the bloodstream from the stomach or intestine. Also desired is the increase in overall stability of the component or components and increase in circulation time in the body. An example of such a moiety is polyethylene glycol or PEG.

For the component (or derivative) the location of release may be the stomach, the small intestine (the duodenum, the jejunum, or the ileum), or the large intestine. One skilled in the art has available formulations that will not dissolve in the stomach, yet will release the material in the duodenum or elsewhere in the intestine. Preferably, the release will avoid the deleterious effects of the stomach environment, either by protection of the protein (or derivative) or by release of the biologically active material beyond the stomach environment, such as in the intestine.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Binders also may be used to hold the therapeutic agent together to form a hard tablet and include materials from natural products such as acacia, tragacanth, starch and gelatin.

An anti-frictional agent may be included in the formulation of the therapeutic to prevent sticking during the formulation process. Lubricants may be used as a layer between the therapeutic and the die wall. Glidants that might improve the flow properties of the drug during formulation and to aid rearrangement during compression also might be added. The glidants may include starch, talc, pyrogenic silica and hydrated silicoaluminate.

In addition, to aid dissolution of the therapeutic into the aqueous environment a surfactant might be added as a wetting agent. Additives which potentially enhance uptake of the protein (or derivative) are for instance the fatty acids oleic acid, linoleic acid and linolenic acid.

Nasal delivery of the immunosuppressant protein or derivative thereof is also contemplated. Nasal delivery allows the passage of the protein to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

Transdermal administration. Various and numerous methods are known in the art for transdermal administration of a drug, e.g., via a transdermal patch. Transdermal patches are described in for example, U.S. Pat. No. 5,407,713, issued Apr. 18, 1995, to Rolando et al.; U.S. Pat. No. 5,352,456, issued Oct. 4, 1994, to Fallon et al.; U.S. Pat. No. 5,332,213 issued Aug. 9, 1994, to D'Angelo et al.; U.S. Pat. No. 5,336,168, issued Aug. 9, 1994, to Sibalis; U.S. Pat. No. 5,290,561, issued Mar. 1, 1994, to Farhadieh et al.; U.S. Pat. No. 5,254,346, issued Oct. 19, 1993, to Tucker et al.; U.S. Pat. No. 5,164,189, issued Nov. 17, 1992, to Berger et al.; U.S. Pat. No. 5,163,899, issued Nov. 17, 1992, to Sibalis; U.S. Pat. Nos. 5,088,977 and 5,087,240, both issued Feb. 18, 1992, to Sibalis; U.S. Pat. No. 5,008,110, issued Apr. 16, 1991, to Benecke et al.; and U.S. Pat. No. 4,921,475, issued May 1, 1990, to Sibalis, the disclosure of each of which is incorporated herein by reference in its entirety.

It can be readily appreciated that a transdermal route of administration may be enhanced by use of a dermal penetration enhancer, e.g., such as enhancers described in U.S. Pat. No. 5,164,189 (supra), U.S. Pat. No. 5,008,110 (supra), and U.S. Pat. No. 4,879,119, issued Nov. 7, 1989, to Aruga et al., the disclosure of each of which is incorporated herein by reference in its entirety.

Pulmonary Delivery. Also contemplated herein is pulmonary delivery of the pharmaceutical compositions of the present invention. A pharmaceutical composition of the present invention is delivered to the lungs of a mammal while inhaling and traverses across the lung epithelial lining to the blood stream. Other reports of this include Adjei et al. [Pharmaceutical Research, 7:565-569 (1990); Adjei et al., International Journal of Pharmaceutics, 63:135-144 (1990) (leuprolide acetate); Braquet et al., Journal of Cardiovascular Pharmacology, 13(suppl. 5): 143-146 (1989) (endothelin-1); Hubbard et al., Annals of Internal Medicine, Vol. III, pp. 206-212 (1989) (.alpha. 1-antitrypsin); Smith et al., J. Clin. Invest., 84:1145-1146 (1989) (.alpha.-1-proteinase); Oswein et al., "Aerosolization of Proteins", Proceedings of Symposium on Respiratory Drug Delivery II, Keystone, Colo., March, (1990) (recombinant human growth hormone); Debs et al., J. Immunol., 140:3482-3488 (1988) (interferon $\gamma$ and tumor necrosis factor $\alpha$); Platz et al., U.S. Pat. No. 5,284,656 (granulocyte colony stimulating factor)]. A method and composition for pulmonary delivery of drugs for systemic effect is described in U.S. Pat. No. 5,451,569, issued Sep. 19, 1995, to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. With regard to construction of the delivery device, any form of aerosolization known in the art, including but not limited to spray bottles, nebulization, atomization or pump aerosolization of a liquid formulation, and aerosolization of a dry powder formulation, can be used in the practice of the invention.

All such devices require the use of formulations suitable for the dispensing of pharmaceutical composition of the present invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified pharmaceutical composition of the present invention may also be prepared in different formulations depending on the type of chemical modification or the type of device employed.

Formulations suitable for use with a nebulizer, either jet or ultrasonic, may typically comprise pharmaceutical composition of the present invention (or derivative) dissolved in water at a concentration of e.g., about 0.1 to 25 mg of biologically active ingredients of a pharmaceutical composition of the present invention per mL of solution. The formulation may also include a buffer and a simple sugar (e.g., for stabilization and regulation of osmotic pressure of a pharmaceutical composition of the present invention). The nebulizer formulation may also contain a surfactant, to reduce or prevent surface induced aggregation of the pharmaceutical composition of the present invention caused by atomization of the solution in forming the aerosol.

The liquid aerosol formulations contain a pharmaceutical composition of the present invention and a dispersing agent in a physiologically acceptable diluent. The dry powder aerosol formulations of the present invention consist of a finely divided solid form of a pharmaceutical composition of the present invention and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The term "aerosol particle" is used herein to describe the liquid or solid particle suitable for nasal or pulmonary administration, i.e., that will reach the mucous membranes. Other considerations, such as construction of the delivery device, additional components in the formulation, and particle characteristics are important. These aspects of nasal or pulmonary administration of a drug are well known in the art, and manipulation of formulations, aerosolization means and construction of a delivery device require at most routine experimentation by one of ordinary skill in the art.

Often, the aerosolization of a liquid or a dry powder formulation for inhalation into the lung will require a propellant. The propellant may be any propellant generally used in the art. Specific non-limiting examples of such useful propellants are a chiorofluorocarbon, a hydrofluorocarbon, a hydrochlorofluorocarbon, or a hydrocarbon, including trifluoromethane, dichlorodifluoromethane, dichlorotetrafluoroethanol, and 1,1,1,2-tetrafluoroethane, or combinations thereof.

Systems of aerosol delivery, such as the pressurized metered dose inhaler and the dry powder inhaler are disclosed in Newman, S. P., Aerosols and the Lung, Clarke, S. W. and Davia, D. editors, pp. 197-22 and can be used in connection with the present invention.

Liquid Aerosol Fornulations. The present invention provides aerosol formulations and dosage forms. In general such dosage forms contain a pharmaceutical composition of the present invention in a pharmaceutically acceptable diluent. Pharmaceutically acceptable diluents include but are not limited to sterile water, saline, buffered saline, dextrose solution, and the like.

The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for pH maintenance, solution stabilization, or for the regulation of osmotic pressure. Aerosol Dry Powder Formulations. It is also contemplated that the present aerosol formulation can be prepared as a dry powder formulation comprising a finely divided powder form of pharmaceutical composition of the present invention and a dispersant. Formulations for dispensing from a powder inhaler device will comprise a finely divided dry powder containing pharmaceutical composition of the present invention (or derivative) and may also include a bulking agent, such as lactose, sorbitol, sucrose, or mannitol in amounts which facilitate dispersal of the powder from the device, e.g., 50 to 90% by weight of the formulation. The pharmaceutical composition of the present invention (or derivative) should most advantageously be prepared in particulate form with an average particle size of less than 10 mm (or microns), most preferably 0.5 to 5 mm, for most effective delivery to the distal lung.

In a further aspect, recombinant cells that have been transformed with a nucleic acid encoding the immunosuppressant protein, an active fragment thereof or a derivative thereof and that express high levels of the polypeptide can be transplanted in a subject in need of immunosuppression. Preferably autologous cells transformed with ISP are transplanted to avoid rejection; alternatively, technology is available to shield non-autologous cells that produce soluble factors within a polymer matrix that prevents immune recognition and rejection.

Methods of Treatment, Methods of Preparing a Medicament. In yet another aspect of the present invention, methods of treatment and manufacture of a medicament are provided. Conditions alleviated or modulated by the administration of the present derivatives are those indicated above.

Dosages. For all of the above molecules, as further studies are conducted, information will emerge regarding appropriate dosage levels for treatment of various conditions in various patients, and the ordinary skilled worker, considering the therapeutic context, age and general health of the recipient, will be able to ascertain proper dosing. In addition, where appropriate, the size of the tumor may be relevant.

A subject in whom administration of ISP or an active fragment thereof or a derivative thereof or an analog thereof, is an effective therapeutic regimen is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

In addition to rational design of agonists and antagonists based on the structure of immunosuppressive protein of the present invention further contemplates an alternative method for identifying specific antagonists or agonists and mimics using various screening assays known in the art.

Accordingly, any screening technique known in the art can be used to screen for agonists, antagonists or mimics of ISP. The present invention contemplates screens for small molecules (i.e. compounds being less than 3 Kd) or analogs and mimics, as well as screens for natural analogs that bind to and agonize or antagonize HISP in vivo or mimic the role of HISP as an immune suppressor. For example, natural products libraries can be screened using assays of the invention for molecules that agonize, antagonize, or mimic HISP activity.

Knowledge of the primary sequence of HISP can also provide clue as the inhibitors, antagonists, or mimics of the protein. Identification and screening of antagonists for example is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, Science 249:386-390 (1990); Cwirla, et al., Proc. Natl. Acad. Sci., 87:6378-6382 (1990); Devlin et al., Science, 249:404-406 (1990)], very large libraries can be constructed (10 6-10.sup.8 chemical entities). A second approach uses primarily chemical methods, of which the Geysen method [Geysen et al., Molecular Immunology 23:709-715 (1986); Geysen et al. J. Immunologic Method 102:259-274 (1987)] and the method of Fodor et al. [Science 251:767-773 (1991)] are examples. Furka et al. [14th International Congress of Biochemistry, Volume 5, Abstract FR:013 (1988); Furka, Int. J. Peptide Protein Res. 37:487-493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., Proc. Natl. Acad. Sci. USA 90:107004 (1993); Ohlmeyer et al., Proc. Natl. Acad. Sci. USA 90:10922-10926 (1993); Lam et al., International Patent Publication No. WO 92/00252; Kocis et al., International Patent Publication No. WO 9428028, each of which is incorporated herein by reference in its entirety], and the like can be used to screen for mimics for HISP according to the present invention.

Alternatively, assays for agents that promote immunosuppression can be performed. The agents can be provided readily as recombinant or synthetic polypeptides, for example.

The screening can be performed with cells that have been designed and/or selected for not expressing HISP. For example, the ability of such cells to undergo apoptosis can be determined in the presence of agents which are contained in a screening library, as described in the foregoing references. The agents can be selected for inducing such apoptosis.

In one example, a phage library can be employed. Phage libraries have been constructed which when infected into host E. coli produce random peptide sequences of approximately 10 to 15 amino acids [Parmley and Smith, Gene, 73:305-318 (1988), Scott and Smith, Science, 249:386-249 (1990)]. Specifically, the phage library can be mixed in low dilutions with permissive E. coli in low melting point LB agar which is then poured on top of LB agar plates. After incubating the plates at 37.degree. C. for a period of time, small clear plaques in a lawn of E. coli will form which represents active phage growth and lysis of the E. coli. A representative of these phages can be absorbed to nylon filters by placing dry filters onto the agar plates. The filters can be marked for orientation, removed, and placed in washing solutions to block any remaining absorbent sites. The filters can then be placed in a solution containing, for example, a radioactive fragment of HISP containing most or all of its expressed coding region. After a specified incubation period, the filters can be thoroughly washed and developed for autoradiography. Plaques containing the phage that bind to the radioactive HISP fragment can then be identified. These phages can be further cloned and then retested for their ability to hinder T lymphocyte activation, for example. Once the phages have been purified, the binding sequence contained within the phage can be determined by standard DNA sequencing techniques. Once the DNA sequence is known, synthetic peptides can be generated which represent these sequences.

The effective peptide(s) can be synthesized in large quantities for use in vivo models and eventually in humans to act as tumor suppressors. It should be emphasized that synthetic peptide production is relatively non-labor intensive, easily manufactured, quality controlled and thus, large quantities of the desired product can be produced quite cheaply. Similar combinations of mass produced synthetic peptides have recently been used with great success [Patarroyo, Vaccine, 10:175-178 (1990)].

Example 1

Production of Ntera2/D1

Ntera2/D1 cells (Layton Bioscience, Inc., Sunnyvale, Calif.) were maintained in Dulbecco's minimal essential medium with nutrient mixture F-12 (DMEM/F-12) with 2 mM L-glutamine, 100 U/ml penicillin, 100 µg/ml streptomycin, and 10% (v/v) heat-inactivated fetal bovine serum (FBS) (Life Technologies, Gaithersburg, Md.), and incubated in a 37° C., humidified, 5% $CO_2$ environment.

Example 2

Differentiation to hNT Neurons

Differentiation of Ntera2/D1 is described in detail by Andrews, 1984 and Pleasure et al., 1992, which are hereby incorporated by reference. Briefly, Ntera2/D1 (2.times. 10⁶) were treated with 10 µM all-trans retinoic acid (Sigma, St. Louis, Mo.) for 5-6 weeks. Mitotic non-neuronal cells were inhibited with 1 µM cytosine β-D-arabinofuranoside, 10 µM 5-fluoro-2'-deoxyuridine, and 10 µM 1-β-D-ribofuranosyluracil (Sigma) for 1 week. Some retinoic acid-treated Ntera2/D1 cultures were exposed to 25 Gy γ-irradiation ($^{137}$Cs) to inhibit non-neuronal cells and were not treated with mitotic inhibitors, to ensure that trace amounts of mitotic inhibitors were not contributing to the immunosuppressive properties of hNT supernatant. Differentiated hNT neurons overlying the mixed cell culture were treated with 0.025% trypsin and 0.01% EDTA, dislodged, and replated at a density of 2–3×10⁶ cells/ml in serum-free Opti-Mem medium (Gibco-BRL), or DMEM/F-12 10% FBS medium, each supplemented with 100 U/ml penicillin, 100 µg/ml streptomycin, and 2.0 mM L-glutamine, in flasks pretreated with poly-D-lysine (Sigma) and coated with MATRIGEL® basement membrane matrix (Collaborative Research/Becton Dickinson, Bedford, Mass.). Cultures were fed serum-free Opti-Mem medium or DMEM/F-12 10% FBS medium for up to 6 days, yielding hNT supernatant which was filter sterilized and stored at −20° C. for future analysis. These enriched hNT neuronal cultures consisted of >90% neurons.

Some hNT neurons were cultured 4 days in the presence of 0.5 or 1.0 µM d, 1-threo-1-phenyl-2-hexadecanoylamino-3-pyrrolidino-1-propanol (Matreya, Inc., Pleasant Gap, Pa.), a potent inhibitor of glucosylceramide synthase and ganglioside shedding (Olshefski and Ladisch, 1998; Felding-Habermann et al., 1990). An aliquot of hNT supernatant was collected after the 4-day exposure. hNT neurons were washed, suspended in fresh serum-free Opti-Mem medium, and aliquots of hNT supernatant saved at 24, 48, and 72 hrs post-washing. Each aliquot was analyzed for antiproliferative activity.

Some hNT neurons were cultured in the presence of 1.2 mg/ml N-g-monomethyl-L-arginine (Schweizerhall, Inc., Piscataway, N.J.), an inhibitor of nitric oxide synthase for 3 days and the hNT supernatant analyzed for antiproliferative activity.

Supernatant from other cultures of human NCCIT embryonal carcinoma cells, T98G glioblastoma cells, or THP-1 monocytic leukemia cells (ATCC) were also analyzed for anti-proliferative activity, but were found to have very little (each eliciting less than a mean 1.5% suppression of the PHA assay (n=6), data not shown).

Example 3

MHC Genotype & Phenotype

Ntera2/D1 genomic DNA (75-125 ng/µl) was used as template for MHC class I and II analysis by sequence-specific primer polymerase chain reaction (Bunce et al., 1995) in MHC diagnostic plates (Pel-Freez Clinical Systems, Deerbrook Trail, Wis.), and the amplified products analyzed by ethidium bromide stained electrophoresis.

hNT MHC surface expression was detected using a complement-dependent cytotoxic technique in Terasaki tissue typing trays (One Lambda, Inc., Canoga Park, Calif.). Briefly, $2\times10^6$/ml hNT neurons were reacted with MHC antigen-specific monoclonal antibody (mAb) or known antisera, mixed with rabbit complement, ethidium bromide and acridine orange, and the reaction stopped by hemoglobin-EDTA. Cell viability was scored, and the MHC phenotype determined. At least 2 mAb or 3 overlapping antisera were used to define each MHC antigen.

The hNT neurons express MHC class I proteins. The amplified products of polymerase chain reactions using Ntera2/D1 genomic DNA as template indicated a MHC class I and II genotype of A1 B8 Bw6 Cw7 DR3 DR52 (FIG. 1). The surface expression of MHC molecules on hNT neurons was detected using a complement-dependent cytotoxic technique and limited to the class I proteins A1 B8 Bw6. No surface expression of MHC class II proteins was detected on hNT neurons.

Example 4

Isolation of PBMC

Peripheral blood mononuclear cells (PBMC) were isolated from the blood of healthy human donors by layering over Accu-Prep (Accurate Chemical Corp., Westbury, N.Y.). The interface band was collected, washed, then suspended in either scrum-free Opti-Mem medium, or in RPM1-1640 with 10% FBS supplemented with 100 U/ml penicillin, 100 γg/ml streptomycin and 2.0 mM L-glutamine (RPMI medium with 10% FBS).

Mixed Lymphocyte and Mixed Lymphocyte-Neuron Cultures. Mixed lymphocyte cultures (MLC) consisted of $10^5$ responder and $10^5$ allogeneic stimulator PBMC. Mixed lymphocyte-neuron cultures (MLNC) consisted of 10.sup.5 responder PBMC and 10.sup.5 stimulator hNT neurons. MLC or MLNC were established in triplicates, incubated for 4 days, pulsed with $^3$H-thymidine (3H-TdR), harvested (Packard Instrument, Meriden, Conn.), and counted in a β-spectrometer (Packard Instrument). The uptake of $^3$H-TdR by stimulator cells was prevented by prior 25 Gy γ-irradiation ($^{137}$Cs). The stimulation index of responder PBMC was determined by dividing the mean cpm of triplicate stimulated cultures by the mean cpm of triplicate control syngeneic cultures. Assays were prepared using serum-free Opti-Mem medium, RPMI medium with 10% FBS, or a 1:2 final dilution of hNT supernatant using either medium. Viability of PBMC in MLC and MLNC was assured by trypan blue dye exclusion on day 4.

hNT neurons do not stimulate PBMC proliferation. We first tested the immunogenic potential of hNT neurons in vitro, by mixing hNT neurons with allogeneic PBMC, and assessing for the DNA synthesis and proliferation of lymphocytes. In control MLCs involving 6 separate donors, responder PBMC proliferated in the presence of unmatched, irradiated stimulator PBMC. with a mean stimulation index of 9.4±7.9 (n=16). In spite of the surface expression of MHC class I proteins on hNT neurons, irradiated hNT neurons did not induce responder PBMC to proliferate in MLNC (FIG. 2A). hNT neurons were derived from Ntera2/D cultures treated with RA, and exposed to either mitotic inhibitors or to 25 Gy γ-irradiation ($^{137}$Cs) to eliminate non-neuronal cell growth. In either case, hNT neurons did not induce responder PBMC from 4 separate donors to proliferate, with a mean stimulation index of only 0.2±0.1 (n=12), significantly less than compared to control MLCs (p<0.01). Viability of PBMC in MLNC on day 4 was comparable to that of PBMC in control MLC, and routinely >90% in trypan blue dye exclusion assays.

hNT supernatant suppresses allogeneic MLC. To determine whether this absence of PBMC proliferation in the presence of hNT neurons was attributable to a soluble factor expressed by hNT neurons, we added supernatant from hNT cultures to allogeneic MLC so that the resultant concentration of hNT supernatant was 1:2. hNT supernatant from cultures maintained with or without serum, and treated earlier with either mitotic inhibitors or .gamma.-irradiation to eliminate non-neuronal cell growth, suppressed the proliferation of responder PBMC in allogeneic MLCs by more than 98% compared to control MLC (p<0.01), with a mean stimulation index of only 0.1±0.1 (n=9) (FIG. 2A). Viability of PBMC in MLC on day 4, cultured in either control medium or in the presence of 1:2 hNT supernatant, was comparable, and >90% as indicated by trypan blue dye exclusion.

Example 5

T-Cell Proliferation and IL-2 Production

The accessory cell-dependent mitogens PHA at 1:50 or 1:250, or concanavalin A at 1:20, which cross-link the T-cell receptor, were used to activate triplicate cultures of 105

PBMC. Assays were prepared using serum-free Opti-Mem medium, RPMI medium with 10% FBS, or 1:2 hNT supernatant, incubated for 48 hours, pulsed, harvested, and the uptake of $^3$H-TdR determined. Viability of PHA-stimulated PBMC was assured by trypan blue dye exclusion on day 2.

Recombinant human IL-2 (rhIL-2) (R&D Systems, Minneapolis, Minn.) at 5-500 ng/ml was added to some PHA-stimulated PBMC cultures either 1 hr prior to, upon, or 24 hrs after addition of PHA.

Phorbol 12-myristate 13-acetate (PMA) can bind directly to and activate protein kinase C, leading to DNA synthesis and T-lymphocyte proliferation. Calcium ionophores such as ionomycin can increase the cytosolic calcium concentration of T-cells and lead to T-cell division. PMA and ionomycin act synergistically to stimulate IL-2 production and the proliferation of T-cells independent of an accessory cell influence. PMA at 10 ng/ml and ionomycin at 100 ng/ml were used to activate triplicate cultures of 10.sup.5 PBMC. Assays were prepared using either serum-free Opti-Mem medium, or 1:2 hNT supernatant, incubated, pulsed, harvested, and the uptake of $^3$H-TdR determined.

The influence of hNT supernatant on the production of IL-2 was determined by comparing IL-2 levels in the supernatant of PHA-stimulated PBMC cultures containing either Opti-Mem medium or 1:2 hNT supernatant. Expressed levels of IL-2 prior to, and 4, 15, 24, and 48 hours after PHA stimulation were determined by ELISA (R&D Systems).

The hNT supernatant suppresses T-cell proliferation and IL-2 production. hNT supernatant with or without serum, from cultures treated earlier with either mitotic inhibitors or γ-irradiation to eliminate non-neuronal cell growth, significantly suppressed PHA-stimulated proliferation 87±12% (n=20), and concanavalin A-stimulated proliferation 79±19% (n=8), each (p<0.01) (FIG. 2B). Dilutions of hNT supernatant suppressed PHA-stimulated proliferation in a dose-dependent manner, when tested at 1:2, 1:20, and 1:200 final concentrations, causing a mean 93%, 62%, and 21% suppression, respectively. That hNT supernatant could also block ongoing T-cell proliferation was demonstrated by adding hNT supernatant up to 48 hrs after PHA stimulation, with a mean suppression of 84.+–0.1% (n=6). This suppression of mitogen-driven proliferation of PBMC by hNT supernatant was mediated without a reduction in PBMC viability, determined 2 days after PHA stimulation, with >90% cells viable by trypan blue exclusion.

Control PHA-stimulated cultures of PBMC expressed 621±41 pg/ml IL-2, 48 hours after mitogen stimulation. In contrast, PHA-stimulated PBMC cultured in the presence of hNT supernatant expressed less IL-2, with mean IL-2 levels detected by ELISA at 48 hours post-stimulation of only 223±111 pg/ml (p<0.01) (FIG. 3).

Adding supplemental IL-2 to the PHA-stimulated assay did not activate the "quiescent" PBMC cultured in the presence of hNT supernatant. As expected, when 5-50 ng/ml rhIL-2 was added to control assays 1 hr before PHA stimulation, T-cell proliferation was increased a mean 47±12% (n=2) above levels induced by PHA alone (FIG. 2B). In contrast, adding supplemental rhIL-2 did not reverse the T-cell suppressive activity of the hNT supernatant, which persisted in suppressing the proliferation of PHA-stimulated PBMC a mean 97±3% (n=3) (p<0.01) (FIG. 2B).

PHA activation of T-cell proliferation results in cross-linkage of the T-cell receptor-CD3 (TCR-CD3) complex and is influenced by accessory cell signals. To determine whether hNT supernatant could suppress the direct activation of T-cells by PMA or ionomycin, independent of an accessory cell influence and independent of TCR-CD3 interactions, hNT supernatants were added to PBMC cultures stimulated with 10 ng/ml PMA, or 100 ng/ml ionomycin, or both. hNT supernatant consistently and significantly suppressed the direct activation of T-cell proliferation by PMA, ionomycin, or both by 99±1% (n=3), each (p<0.001).

Example 6

Cell Cycle Analysis

To further demonstrate that hNT supernatant did not lower PBMC viability in immunoassays, propidium iodide stained PBMC were evaluated by flow cytometry, 48 and 72 hrs after PHA-stimulation. PBMC were stimulated with PHA in Opti-Mem medium or 1:2 NT2N-CM, harvested at 48 or 72 hrs, washed, stained with the nucleic acid binding dye propidium iodide (Sigma), and analyzed for DNA content by flow cytometry (fluorescence intensity at 600-650 nm). The proportion of cells in each distinct phase of the cell cycle was calculated with ModFit LT 2.0 software (Verity Software House, Topsham, Minn.).

Cell cycle analysis revealed that hNT supernatant did not reduce PBMC viability compared to controls (90.8±1.7%), that hNT supernatant held PHA-stimulated PBMC in a growth arrested, $G_0/G_1$ phase (97±2%), and that the proportion of PBMC in either the S phase or $G_2$/M phase was reduced by as much as 92% to a mean of only 1.5±0.7% (n=2). The proportions of PBMC undergoing apoptosis, necrosis, and the amount of cellular debris in the modeled events were not different regardless of treatment.

Example 7

Detection and Immunoprecipitation of TGF-β

The hNT supernatant was tested for the presence of TGF-β (R&D Systems) and interleukin-10 by ELISA (Genzyme, Cambridge, Mass.), and for prostaglandin-E2α, vasoactive intestinal peptide (Peninsula Labs, Inc., San Carlos, Calif.), and α-melanocyte stimulating hormone (Phoenix Pharmaceuticals, Belmont. Calif.) by EIA.

To remove TGF-β from hNT supernatant, neutralizing anti-TGF-β mAb 240 at 0.5-10.0 µg/ml (R&D Systems) was added and reacted overnight at 4° C. under rotating conditions. An excess of protein G Sepharose (Amersham Pharmacia Biotech, Piscataway, N.J.) was added, and reacted for 10 hours at 4° C. The mixture was centrifuged at 2000×g for 10 minutes, and the supernatant tested for anti-proliferative activity. Immunoprecipitation of TGF-β was verified by ELISA. In other experiments, 0.01-10.0 µg/ml neutralizing anti-TGF-β mAb 240 was added directly to PHA-stimulated PBMC assays.

We confirmed that purified TGF-β at concentrations detected in some samples of hNT supernatant (100-1000 pg/ml), could suppress proliferation of the IL-2- and IL-4-dependent helper T-cell line HT-2 (Ho et al., 1987) by a mean 40±3.5%, but this TGF-β-mediated suppression was less than the 90±9% suppression mediated by the hNT supernatant (n=3) (p<0.01) (data not shown). We also confirmed that 0.1-0.4 µg/ml mAb 240 could neutralize 53% of the antiproliferative effect of 250 µg/ml purified TGF-β on HT-2 cells, reducing it from 40±3.5% to 19±3% suppression (n=3) (data not shown). In contrast, as described below, immunoprecipitation of TGF-β did not reduce the suppressive activity of the hNT supernatant.

Although TGF-β was detected in 81% of hNT supernatant aliquots at a mean level of 753±512 pg/ml, aliquots of hNT supernatant without detectable TGF-β (threshold >0.1 ng/ml) fully suppressed the PHA assay 94.+−0.5% (n=3), data not shown. TGF-β was removed from samples of hNT supernatant using a neutralizing anti-TGF-β mAb and an excess of protein G Sepharose. Complete immunoprecipitation of TGF-β, verified by ELISA, did not reduce the immunosuppressive activity of the hNT supernatant, with 97±3% suppression of the PHA assay prior to immunoprecipitation, and 93±1% suppression after TGF-β immunoprecipitation (n=5), data not shown. In other experiments, addition of 0.01-10.0 μg/ml neutralizing anti-TGF-β mAb 240 directly to the PHA assay did not alter the suppressive activity of the hNT supernatant, with 97±1% suppression of the PHA assay retained with mAb treatment (n=7).

Example 8

Characterization of the hNT Immunosuppressive Protein hNT supernatant was concentrated using ultrafiltration (YM10, Amicon, Danvers, Mass.) and fractionated using Sephacryl S-300 HR gel in a 2.5×95 cm column (Amersham Pharmacia Biotech). Each 4 ml fraction was assessed for protein content at 280 nm. Groups of five fractions were pooled, diluted 1:20, and tested for ability to suppress PHA-induced PBMC proliferation.

hNT supernatant, or the immunosuppressive gel filtration fractions, were treated with either heat (56° C. for 30 minutes), or to pH 2 or pH 11, or mixed with trypsin- or carboxypeptidase A-coated agarose beads (Sigma) each for 60 minutes, or incubated with *Vibrio cholerae* neuraminidase-coated agarose beads (Sigma) for 2 hours to eliminate gangliosides, then evaluated and tested for retained suppressive activity in a PHA-stimulated assay.

To determine whether the antiproliferative factor(s) could bind to affinity resins, either 250 mg/mi Heparin-Sepharose CL-B gel, or Blue Sepharose gel (Amersham Pharmacia Biotech) were separately combined with either hNT supernatant or the active gel filtration fractions at ratios of 1:1 to 4:1. Each separate mixture was centrifuged, and the supernatants and washes containing unbound proteins were retained for analysis. The bound protein was eluted from each gel with 0.25 M-1.5 M NaCl. Eluted fractions were desalted with PD-10 Desalting Columns (Amersham Pharmacia Biotech). The unbound and eluted fractions were tested for retained suppressive activity in PHA-stimulated assays.

Active gel filtration fractions were also tested for binding to Sepharose Fast Flow resins comprised of weak (DEAE) and strong (Q) anion exchangers, and weak (CM) and strong (SP) cation exchangers (Pharmacia Biotech). Bound fractions were removed from exchange resins using 0.25-1.5 M NaCl in 50 mM HEPES buffer. The eluted fractions were dialyzed against 0.15 M NaCl in 0.5 M HEPES. The unbound fraction and eluted fractions were each tested for suppression of PHA-induced T-cell proliferation.

The peak active gel filtration fraction was used for isoelectric focusing using the Bio-Rad Rotofor system, and a broad (pH 3-10) ampholyte range, followed by a narrow (pH 4-6) ampholyte range. After focusing with 1.5 ml ampholyte (pH 4-6, 40% w/v) and 45.5 ml doubly distilled water for 60 minutes at 15 watts and 4° C., the active isoelectric fraction was identified. This active isoelectric fraction at 2.1 mg in a 3.0 ml volume was then focused for an additional 3 hours using the same conditions. Ampholytes were removed by the addition of 0.25 ml of 5 M NaCl per ml, and fractions were exhaustively dialyzed against 50 mM HEPES, pH 7.2, containing 150 mM NaCl for 22 hours at 4° C. Immunosuppressive activity was detected using the PHA-stimulated assay.

hNT neurons were cultured for 4 days in the presence of 0.5 or 1.0 μM d, 1-threo-1-phenyl-2-hexadecanoylamino-3-pyrrolidino-1-propanol, a potent inhibitor of glucosylceramide synthase and ganglioside shedding. An aliquot of hNT supernatant was collected after the 4-day exposure, neurons were washed, suspended in fresh medium, and aliquots of hNT supernatant saved at 24, 48, and 72 hrs post-washing. In spite of this ganglioside-inhibiting treatment of neuron cultures, the suppressive activity of the hNT supernatant was retained, with 93±10% inhibition of the PHA assay (n=4), data not shown.

hNT neurons were cultured in the presence of 1.2 mg/ml N-g-monomethyl-L-arginine, an inhibitor of nitric oxide synthase, for 3 days and found that the suppressive activity of the hNT supernatant was fully retained (data not shown).

No evidence was found indicating that the hNT supernatant had T-cell suppressive levels of prostaglandin-E2α (assay threshold of >39 pg/ml), α-melanocyte stimulating hormone (>1.3 ng/ml), vasoactive intestinal peptide (>0.7 ng/ml), or IL-10 (>8.5 pg/ml).

These findings encouraged efforts to concentrate, characterize, and purify the suppressive activity of hNT supernatant. The PHA-activated T-cell proliferation assay was used as a simple and reliable indicator of T-cell reactivity. As shown in Table 1, hNT supernatant lost most of its suppressive activity when heated or exposed to low pH 2, or treated with carboxypeptidase A. hNT supernatant exposed to high pH 11, or treated with trypsin retained approximately 48% residual T-cell suppressive activity. The antiproliferative activity of hNT supernatant did not bind to Heparin-Sepharose CL-B gel, with unbound fractions suppressing T-cell proliferation a mean 99±0% (n=5).

hNT supernatant was concentrated using YM10 ultrafiltration, and the concentrate fractionated using a Sephacryl S-300 HR gel. Each fraction was assessed for protein content, and pools of five fractions were diluted 1:20 and tested for suppressive activity. Pooled fractions were found to suppress T-cell proliferation over a molecular mass range of approximately 40-100 kDa (FIG. 4). The peak immunosuppressive active fraction had approximately 7.7 μg/ml of total protein.

TABLE 1

Immunosuppressive Properties of hNT Supernatant

| Treatment of hNT Supernatant | Suppression of T-cell Proliferation* |
|---|---|
| None | ++++ |
| 56° C. | + |
| pH 2 | + |
| pH 11 | ++ |
| Trypsin | ++ |
| Carboxypeptidase A | + |
| Heparin Sepharose | ++++ |
| Gel Filtration Fraction ~40-100 KDa | ++++ |
| Treatment of Fraction ~40-100 kDa | |
| Blue Sepharose | ++++ |
| Trypsin | + |
| Carboxypeptidase | + |
| Neuraminadase | ++++ |
| Cation Exchange Resin | ++++ |
| Anion Exchange Resin | + |

*% Suppression of PHA-stimulated PBMC proliferation:
++++, 80-100%; +++, 60-79%; ++, 40-59%; +, 10-39%; −, none.

The antiproliferative activity of the peak active gel filtration fractions was not degraded by exposure to *Vibrio cholerae* neuraminidase-coated agarose beads to eliminate gangliosides (Table 1). In contrast, protease treatments using trypsin or carboxypeptidase eliminated most of the suppressive activity of these fractions (Table 1). Although 79% of the total protein in the peak active fraction bound to the albumin-binding resin Blue Sepharose, the unbound fraction continued to suppress the proliferation of T-cells a mean 75±5% (n=2), suggesting that the immunosuppressive protein expressed by hNT neurons was not carried by albumin.

The peak active fraction was tested for binding to weak or strong anion or cation exchangers. Bound fractions were eluted from exchange resins and dialyzed against HEPES buffer, then bound and unbound fractions were tested for suppressive activity. The T-cell suppressive activity of the peak active fraction consistently bound to anion, but not to cation exchanger resins, indicating a net anionic charge. Unbound fractions of weak (CM) and strong (SP) cation exchange resins continued to suppress T-cell proliferation a mean 77±31% and 99±0%, respectively (n=2) (Table 1). In contrast, unbound fractions of weak (DEAE) anion exchange resin suppressed T-cells only 10±17%, and unbound fractions of strong (Q) anion exchange resin had no residual T-cell suppressive activity (n=3). Bound proteins that were eluted from the anion exchangers suppressed the proliferation of T-cells 99% (data not shown).

We next used the peak active gel filtration fraction for isoelectric focusing. Preliminary broad range isoelectric focusing indicated that the immunosuppresive protein had an isoelectric point of approximately 5. Consequently, we focused the peak active fraction using a narrow ampholyte pH range of 4-6. Of the twenty isoelectric fractions collected, only fraction #10 suppressed either the PHA or PMA/ionomycin-induced proliferation of T-cells more than 70%, each ($p<0.01$) indicating that the hNT immunosuppressive protein had an isoelectric point of 4.8 (FIG. 5).

Current research employs a purification scheme that utilizes preparative polyacrylamide gel electrophoresis of the active isoelectric fraction #10. It incorporates Blue Sepharose removal of albumin whose isoelectric point of 4.9 causes it to elute in close proximity to the active protein, and the concentrating effect of Q Sepharose columns using 50 mM ethanolamine pH 9 buffer. We are concurrently testing whether stability of the protein is improved by incorporating the use of β-mercaptoethanol and various concentrations of glycerol in the eluting buffer.

Although others have demonstrated using broad, nonspecific antisera that differentiation of Ntera2/D1 cells to hNT neurons results in the expression of some unspecified MHC class I and β-2 microglobulin molecules (Segars et al., 1993), we determined the specific MHC genotype and phenotype of these cells. In spite of the demonstrated surface expression of MHC class I proteins A1 B8 Bw6, hNT neurons did not activate the proliferation of allogeneic immune cells in vitro. This lack of allogeneic T-lymphocyte activation by hNT neurons was not attributable to low constitutive MHC class I expression on the surface of the hNT neurons, since hNT supernatants potently suppressed T-cell proliferation in a dose-dependent manner.

A unique hNT neuron immunosuppressive protein with a molecular mass of 40-100 kDa, an isoelectric point 4.8, and a net anionic charge was identified. The abrogating effect of this hNT protein on T-cell activation and proliferation was direct, and not mediated through the T-cell receptor-CD3 complex, or via altered accessory cell signals. It caused a significant reduction in the level of IL-2 expressed by T-cells, and supplemental IL-2 could not override its immunosuppressive effect. The quiescent T-cells were viable and arrested in the $G0/G_1$ phase of the cell cycle.

Our initial evaluations of the immunosuppressive properties of the hNT supernatant were guided by precedents, which showed that retinoic acid treatment of other embryonal carcinoma cell lines can increase shedding of gangliosides (Chen et al., 1989; Osanai et al., 1997), or expression of TGF-β (Rizzino et al., 1983), which can be immunosuppressive in vitro.

We developed multiple lines of evidence that dismissed the potential that the hNT immunosuppressive effect could have been attributed to gangliosides shed from the hNT neurons. Inhibition of T-cell proliferation and IL-2 production by ganglioside-enriched supernatants from brain lipid homogenates is found in the lipid-enriched and protein-depleted fraction (Irani et al., 1996; Irani et al., 1997). In contrast, hNT supernatant was used directly in immunoassays, without a selective lipid extraction enriching for gangliosides, and effectively suppressed T-cell proliferation. Pretreating brain ganglioside-enriched supernatant with neuraminidase eliminates the inhibitory effect of the brain-derived supernatant on T-cells (Irani et al, 1997). In contrast, neuraminidase pretreatment of the hNT supernatant peak active gel filtration fraction did not reduce its suppressive effect on T-cell proliferation. Brain tumor cells can shed gangliosides in vitro and in vivo, potentially in monomeric form (<2 kDa), bound to albumin (68 kDa), or as micelles (130 kDa) (Kong et al., 1998; Valentino et al., 1990). In contrast, the T-cell suppressive protein in hNT supernatant ranged in mass between 40-100 kDa, and did not segregate with albumin or other Blue Sepharose-bound proteins. Tumor cell shedding of gangliosides in vitro can be inhibited 83% by culturing cells in the presence of 1.0 μM d, 1-threo-1-phenyl-2-hexadecanoylamino-3-pyrrolidino-1-propanol, an inhibitor of glucosylceramide synthase (Felding-Habermann et al., 1990). In contrast, culturing hNT neurons in the presence of 0.5 or 1.0 μM d, 1-threo-1-phenyl-2-hexadecanoylamino-3-pyrrolidino-1-propanol did not reduce the suppressive effect of hNT supernatant on T-cell proliferation.

Similarly, several lines of evidence dismiss the potential that TGF-.beta. was responsible for the dramatic suppression of T-cell proliferation by hNT supernatant. First, hNT supernatant without detectable levels of TGF-β (threshold >0.1 ng/ml) suppressed T-cell proliferation. Immunoprecipitation of TGF-β from hNT supernatant that had detectable TGF-β levels using neutralizing anti-TGF-β mAb did not substantially reduce the T-cell suppressive activity of the hNT supernatant. Prior reports have shown that although a 1.0 ng/ml dose of TGF-β could suppress 50% of either a PHA or PMA/ionomycin-stimulated T-cell proliferation when added up to 6 hours after stimulation, this suppressive effect of TGF-β was lost 16 hours after T-cell activation (Ahuja et al., 1993). In contrast, hNT supernatant suppressed 84% of a PHA-driven T-cell proliferation, even up to 48 hours after T-cell stimulation. Further, TGF-β is a heparin-binding protein (McCaffrey et al., 1992), but the hNT immunosuppressive protein did not segregate with heparin-bound proteins. Finally, the peak active gel filtration fraction of hNT supernatant that profoundly suppressed T-cell proliferation had no detectable TGF-β by ELISA.

We sought but could find no evidence of other potential co-mediators of the T-cell suppressive effect of the hNT immunosuppressive protein. Although T-cell proliferation in vitro may be modulated by neuropeptides (e.g., vasoactive intestinal peptide) (Sun and Ganea, 1993; Nio et al., 1993), or annexin II (Nygaard et al., 1998), or neurotransmitters (e.g., dopamine) or their metabolites (e.g., homovanillic acid), our evidence suggested that the observed T-cell suppressive effect of hNT neurons and supernatant was attributable to the expression of a single anionic protein with an isoelectric point of 4.8.

Studies of Ntera2/D1 cells and their hNT neuron derivative may contribute to the development of a transfectable and transplantable neuron with both therapeutic and protective features. Assuming that the hNT immunosuppressive protein can modulate immune responsiveness in vivo, then hNT neuron grafts may be both therapeutic and self-protective, either alone or as co-grafts with other cells. hNT neurons may serve as a model of the neuronal regulation of immune privilege within the CNS.

This novel T-lymphocyte suppressive hNT protein has broad applications in preventing graft rejection in transplantation settings, in the treatment of autoimmune diseases, and in the suppression of severe allergic responses. Further, its neuronal origin introduces the likelihood that it may represent a novel class of immunomodulators, which are responsible for the maintenance of CNS immune privilege.

REFERENCES

1. Ahuja, S. S., Paliogianni, F., Yamada, H., Balow, J. E., & Boumpas, D. T. (1993), Effect of Transforming Growth Factor-Beta on Early and Late Activation Events in Human T-cells., J Immunol. 150, 3109-3118.
2. Aloisi, F., Ria, F., Penna, G., & Adorini, L. (1998), Microglia are More Efficient Than Astrocytes in Antigen Processing and in Th1 but not Th2 Cell Activation., J. Immunol. 160, 4671-4680.
3. Andrews, P. W., Dajanov, I., Simon. D., Banting, G. S., Carlin, C, Dracopoli, N. C., & Fogh, J. (1984), Pluripotent Embryonal Carcinoma Clones Derived from the Human Teratocarcinoma Cell Line Tera-2. Differentiation in Vivo and in Vitro., Lab. Invest. 50, 147-162.
4. Andrews, P. W. (1984), Retinoic Acid Induces Neuronal Differentiation of a Cloned Human Embryonal Carcinoma Cell Line in Vitro., Dev Biol. 103, 285-293.
5. Anton, R., Kordower, J. H., Maidment, N. T., Manaster, J. S., Kane, D. J., Rabizadeh, S., Schueller, S. B., Yang, J., Rabizadeh, S., Edwards, R. H, et al., (1994), Neural-Targeted Gene Therapy for Rodent and Primate Hemiparkinsonism., Exp. Neurol. 127, 207-218.
6. Bergelson, L. D. (1995), Serum Gangliosides as Endogenous immunomodulators., Immunol. Today 16, 483-486.
7. Bjorklund, A. (1992), Dopaminergic Transplants in Experimental Parkinsonism: Cellular Mechanisms of Graft-Induced Functional Recovery., Curr. Opin. Neurobiol. 2, 683-689.
8. Borlongan, C. V., Tajima, Y., Trojanowski, J. Q., Lee, V. M. J., & Sanberg, P. R. (1998), Transplantation of Cryopreserved Humn Embryonal Carcinoma-Derived Neurons (NT2N cells) Promotes Functional Recovery in Ischemic Rats., Exp. Neurol. 149, 310-321.
9. Bunce, M, O'Neill, C. M., Barnardo, M. C, Krausa, P., Browning, M. J., Morris, P. J., & Welsh, K. I. (1995), Phototyping: Comprehensive DNA Typing for HLA-A, B, C, DRB1, DRB3, DRB4, DB5, and DQB1 by PCR With 144 Primer Mixes Utilizing Sequence Specific Primers (PCR-SSP)., Tissue Antigens 46, 355-367.
10. Carson, M. J., Reilly, C. R., Sutcliffe, J. G., & Lo, D. (1998), Mature Microglia Resemble Immature Antigen-Presenting Cells., Glia 22, 72-85.
11. Carson, M. J., Reilly, C. R., Sutcliffe, J. G., & Lo, D. (1999), Disproportionate Recruitment of CD8+T-cells into the Central Nervous System by Professional Antigen-Presenting Cells., Am. J. Pathol. 154, 481-494.
12. Carson, M. J. & Sutcliffe, J. G. (1999), Balancing Function vs. Self Defense: The CNS as an Active Regulator of Immune Responses., J. Neurosci. Res. 55, 1-8.
13. Chen, C, Fenderson, B. A., Andrews. P. W., & Hakomori, S. (1989), Glycolipid Glycosyltransferases in Human Embryonal Carcinoma Cells During Retinoic Acid Induced Differentiation., Biochemistry 28, 2229-2238.
14. Cook, D. G., Lee, V. M. Y., & Doms. R. W. (1994), Expression of Foreign Proteins in a Human Neuronal System., Methods in Cell Biology 43, 289-303.
15. Cserr, H. F. & Knopf, P. M. (1992), Cervical Lymphatics, the Blood-Brain Barrier and the Immunoreactivity of the Brain: A New View., Immunol. Today 113, 507-512.
16. Dyatlovitskaya, E. V., & Bergelson, L. D. (1987), Glycosphingolipids and Antitumor Immunity., Biochim. Biophys. Acta. 907, 125-143.
17. Fabry, Z., Raine, C. S., & Hart, M. N. (1994), Nervous Tissue as an Immune Compartment: The Dialect of the Immune Response in the CNS., Immunol. Today 15, 218-224.
18. Fackelmann, K. (1998), Stroke Rescue: Can Cells Injected Into the Brain Reverse Paralysis?, Science News 154, 120-122.
19. Felding-Habermann, B., Igarashi, Y., Fenderson, B. A., Park, L. S., Radin, N. S., Inokuchi, J., Strassmann, G., Handa, K., & Hakomori, S. (1990), A Ceramide Analogue Inhibits T-cell Proliferative Response Through Inhibition of Glycospingolipid Synthesis and Enhancement of N,N-dimethylsphingosine Synthesis., Biochem. 29, 6314-6322.
20. Fisher, L. J., Jinnah, H. A., Kale, L. C, Higgins, G. A., & Gage, F. G. (1991), Survival and Function of Intrastriatally Grafted Primary Fibroblasts Genetically Modified to Produce L-dopa., Neuron 6, 371-380.
21. Goldstein, G. W. & Betz, A. L. (1986), The Blood-Brain Barrier., Sci. Am. 155, 74-83.
22. Hickey, W. F., Hsu, B. L., & Kimura, H. (1991), T-Lymphocyte Entry Into the Central Nervous System., J. Neurosei. Res. 28, 254-260.
23. Ho, S. N., Abraham, R. T., Gillis, S., & McKean, D. J. (1987), Differential Bioassay of Interleukin 2 and Interleukin 4., J. Immunol. Mthds. 98, 99-104.
24. Iacovitti, L., & Stull, N. D. (1997), Expression of Tyrosine Hydroxylase in Newly Differentiated Neurons From a Human Cell Line (hNT)., NeuroReport 8, 1471-1474.
25. Irani, D. N., Lin, K.-I., & Griffin, D. E. (1996), Brain-Derived Gangliosides Regulate the Cytokine Production and Proliferation of Activated T-cells., J. Immunol. 157, 4333-4340.
26. Irani, D. N., Kin, K. I., & Griffin, D. E. (1997), Regulation of Brain-Derived T-cells During Acute Central Nervous System Inflammation., J. Immunol. 158, 2318-2326.
27. Kleppner, S. R., Robinson, K. A., Trojanowski, J. Q., & Lee, V. M. Y. (1995), Transplanted Human Neurons Derived From a Teratocarcinoma Cell Line (Ntera-2) Mature, Integrate, and Survive for Over 1 Year in the Nude Mouse Brain., J. Comp. Neurol. 357, 618-632.
28. Kong, Y., Li, R., & Ladisch, S. (1998), Natural Forms of Shed Tumor Gangliosides., Biochimica Biophysica Acta 1394, 43-56.
29. Kordower, J. H., Freeman, T. B., Snow, B., Vingerhoets, F. J. G., Muffson, E. J., Sanberg, P. R., Hauser, R. A., Smith, D. A., Nauert, G. M., Perl, D. P., & Olanow, C. W. (1995), Neuropathological Evidence of Graft Survival and Striatal Reinnervation After the Transplantation of Fetal Mesencephalic Tissue in a Patient with Parkinson's Disease., N. Engl. J., Med. 332, 1118-1124.
30. Lampson, L. A., & Siegel, G. (1988), Defining the Mechanisms that Govern Immune Acceptance or Rejection of Neural Tissue., Prog. Brain Res. 78, 243-247.
31. Lee, V. M. Y., & Andrews, P. W. (1986), Differentiation of Ntera-2 Clonal Human Embryonal Carcinoma Cells into Neurons Involves the Induction of All Three Neurofilament Proteins., J. Neurosci. 6, 514-521.
32. Mahmood, R., Flanders, K. C, & Morris-Kay, G. M. (1995), The Effects of Retinoid Status on TGF-beta Expression During Mouse Embryogenesis., Anatomy Embryol. 192, 21-33.
33. Massa, P. T. (1993), Specific Suppression of Major Histocompatibility Complex Class I and Class II Genes in Astrocytes by Brain-Enriched Gagliosides., J. Exp. Med. 178, 1357-1363.
34. McCaffrey, T. A., Falcone, D. J., & Du, B. (1992), Transforming Growth Factor Beta-1 in a Heparin Binding Protein: Indentification of Putative Heparin-Binding Regions and Isolation of Heparins With Varying Affinity for TGF-beta 1., J Cell Physiol. 152, 430-440.
35. Nio, D. A., Moylan, R. N., & Roche, J. K. (1993), Modulation of T-Lymphocyte Function by Neuropeptides. Evidence For Their Role as Local Immunoregulatory Elements., J. Immunol. 150, 5281-5288.
36. Nygaard, S. J., Haugland, H. K. Kristoffersen, E. K., Lund-Johansen, M.; Laerum, O. D., & Tysnes, O. B. (1998), Expression and Annexin II in Glioma Cell Lines and in Brain Tumor Biopsies., J. Neuro-Oncol. 38, 11-18.
37. Olshefski, R., & Ladisch, S. (1998), Synthesis, Shedding, and Intercellular Transfer of Human Medulloblastoma Gangliosides: Abrogation by a New Inhibitor of Glucosylceramide Synthase, J. Neurochem. 70, 467-472.
38. Osanai, T., Watanabe, Y., & Sanai, Y. (1997), Glycolipid Sialyltransferases are Enhanced During Neural Differentiation of Mouse Embryonic Carcinoma Cells., Biochem. Biophys. Res. Comm. 241, 327-333.
39. Perlow, M. J., Freed, W. J., Hoffer, B. J., Seiger, A., Olson, L., & Wyatt. R. J. (1979), Brain Grafts Reduce Motor Abnormalities Produced by Destruction of Nigrostriatal Dopamine System., Science 204, 643-647.
40. Pleasure, S. J., Page, C, & Lee, V. M. Y. (1992), Pure, Postmitotic, Polarized Human Neurons Derived From Ntera-2 Cells Provide a System for Expressing Exogenous Proteins in Terminally Differentiated Neurons., J. Neurosci. 12, 1802-1815.
41. Pleasure, S. J., & Lee, V. M. Y. (1993), Ntera-2 Cells: A Human Cell Line Which Displays Characteristics Expected of a Human Committed Neuronal Progenitor Cell., J. Neurosci Res. 35, 585-602.
42. Rail, G. F. (1998), CNS Neurons: The Basis and Benefits of Low Class I Major Histocompatiblity Complex Expression., Curr. Top. Microbiol. Immunol. 232, 115-34.
43. Rizzino, A., Orme, L. S., & De Larco, J. E. (1983), Embryonal Carcinoma Cell Growth and Differentiation. Production of and Response to Molecules With Transforming Growth Factor Activity., Exp. Cell Res. 143, 143-152.
44. Robb, R. J. (1986), The Suppressive Effect of Gangliosides Upon IL2-dependent Proliferation as a Function of Inhibition of IL2-receptor Association., J. Immunol. 136, 971-976.
45. Sabate, O., Horellou, P., Vigne, E., Colin, P., Perricaudet, M., Buc-Caron, M. H., & Mallet, J. (1995), Transplantation to the Rat Brain of Human Neural Progenitors That Were Genetically Modified Using Adenoviruses., Nat. Genet. 9, 256-260.
46. Segars, J. H., Nagata, T., Bours, V., Medin, J. A., Franzoso, G., Blanco, J. C. G., Drew, P. D., Becker, K. G., An, J., Tang, T., Stephany, D. A., Neel, B., Siebenlist, U., & Ozato, K. (1993), Retinoic Acid Induction of Major Histocompatibility Complex Class I Genes in Ntera-2 Embryonal Carcinoma Cells Involves Induction of NF-kappa B (p50-p65) and Retinoic Acid Receptor Beta-Retinoid X Receptor Beta Heterodimers., Mol. Cell. Biology 13, 6157-6169.
47. Sun, L. & Ganea, D. (1993), Vasoactive Intestinal Peptide Inhibits Interleukin (IL)-2 and IL-4 Production Through Different Molecular Mechanisms in T-cells Activated Via T-cell Receptor/CD2 Complex., J. Neuroimmunol. 48, 59-69.
48. Trojanowski, J. Q., Kleppner, S. R., Hartley, R. S., Miyazono, M., Fraser, N. W., Xesari, S., & Lee, V. M. Y. (1997), Transferable and Transplantable Postmitotic Human Neurons: A Potential "Platform" for Gene Therapy of Nervous System Diseases., Exp. Neurol. 144, 92-97.
49. Valentino, L., Moss, T., Olson, E., Wang, H. J.: Elashoff, R., & Ladisch, S. (1990), Shed Tumor Gangliosides and Progression of Human Neuroblastoma., Blood 75, 1564-1567.
50. Weller. M., & Fontana, A. (1995), The Failure of Current Immunotherapy for Malignant Glioma. Tumor-derived TGF-beta, T-cell Apoptosis, and the Immune Privilege of the Brain., Brain Res. Rev. 21, 128-151.
51. Weller, R. O., Engelhardt, B., & Phillips, M. J. (1996), Lymphocyte Targeting of the Central Nervous System: A Review of Afferent and Efferent CNS-Immune Pathways., Brain Pathol. 6, 275-288.
52. Zeller, M, & Strauss, W. L. (1995), Retinoic Acid Induces Cholinergic Differentiation of Ntera-2 Human Embryonal Carcinoma Cells., Int. J. Dev. Neurosci. 13, 437-445.

What is claimed is:

1. An isolated human immunosuppressant protein (HISP) using the steps comprising:
   a) growing a culture of hNT neuronal cells;
   b) obtaining supernatant from the hNT cell culture;
   c) concentrating the supernatant;
   d) exposing the supernatant to gel electrophoresis to produce isoelectric fractions;
   e) collecting a peak immunosuppressive active isoelectric fraction; and f) collecting the protein extract from the fraction wherein the protein extract has an isoelectric point of about 4.8, a molecular weight of 40-100 kDa and exhibits at least one immunosuppressive activity selected from the group consisting of suppressed T-cell activation, suppressed T-cell proliferation, and suppressed production of IL-2 by T-cells.

2. The protein extract of claim 1 isolated using the steps, further comprising: purifying the peak immunosuppressive active isoelectric fraction by removing albumin on an albumin-binding column; and concentrating the active isoelectric fraction on an anionic column; column prior to collecting the protein extract.

3. The protein extract of claim 1, wherein the supernatant is concentrated by ultrafiltration.

4. The protein extract of claim 1, wherein the active isoelectric fraction suppresses T-cell proliferation and suppresses production of IL-2 by T-cells by at least about 70%.

5. An isolated human immunosuppressant protein (HISP) extract using the steps comprising:
   a) growing a culture of hNT neuronal cells;
   b) obtaining supernatant from the hNT neuronal cell culture;
   c) concentrating the supernatant;
   d) exposing the supernatant to gel electrophoresis to produce isoelectric fractions;
   e) purifying an isoelectric fraction exhibiting peak immunosuppressive activity; and
   f) collecting the protein extract having a molecular weight of 40-100 kDa and an isoelectric point of about 4.8 from the fraction wherein the protein extract exhibits at least one immunosuppressive activity selected from the group consisting of suppressed T-cell activation, suppressed T-cell proliferation, and suppressed production of IL-2 by T-cells.

6. The protein extract of claim 5, wherein the supernatant is concentrated by ultrafiltration.

7. The protein extract of claim 5, wherein the active isoelectric fraction suppresses T-cell proliferation and suppresses production of IL-2 by T-cells by at least about 70%.

8. The protein extract of claim 5 wherein the isoelectric fraction is purified by removing albumin through the use of an albumin-binding column.

9. The protein extract of claim 5 isolated using the steps, further comprising: concentrating the active isoelectric fraction on an anionic column prior to collecting the protein extract.

10. An isolated human immunosuppressant protein (HISP) extract using the steps comprising:
    a) obtaining supernatant from hNT neuronal cell culture;
    b) concentrating the supernatant using ultrafiltration;
    c) exposing the supernatant to preparative polyacrylamide gel electrophoresis to produce isoelectric fractions;
    d) collecting a peak immunosuppressively active isoelectric fraction wherein immunosuppression is determined by PHA-stimulated assay;
    e) purifying the active isoelectric fraction by removing albumin on an albumin-binding column;
    f) concentrating the active isoelectric fraction on an anionic column; and
    g) collecting the isolated protein extract having an isoelectric point of about 4.8, a molecular weight of about 40-100 kDa and exhibits at least one immunosuppressive activity selected from the group consisting of suppressed T-cell activation, suppressed T-cell proliferation, and suppressed production of IL-2 by T-cells.

11. The protein extract of claim 10, wherein the active isoelectric fraction suppresses T-cell proliferation and suppresses production of IL-2 by T-cells by at least about 70%.

12. The protein extract of claim 10, further comprising treating the isoelectric fractions obtained in step d by a method selected from the group consisting of exposing the fractions to pH 11 environment, and incubating the fraction with *Vibrio cholerae* neuraminidase-coated agarose beads for 2 hours.

* * * * *